United States Patent [19]

Houlihan et al.

[11] 3,982,020

[45] Sept. 21, 1976

[54] SUBSTITUTED BENZYLIDENE HYDRAZINES FOR TREATING HYPERGLYCEMIA, OBESITY AND INFLAMMATION

[75] Inventors: William J. Houlihan; Robert E. Manning, both of Mountain Lakes, N.J.

[73] Assignee: Sandoz, Inc., E. Hanover, N.J.

[22] Filed: Sept. 5, 1972

[21] Appl. No.: 286,320

Related U.S. Application Data

[60] Division of Ser. No. 20,418, March 17, 1970, abandoned, which is a continuation-in-part of Ser. No. 825,412, May 16, 1969, abandoned.

[52] U.S. Cl. .................................. 424/326; 424/327
[51] Int. Cl.² ...................................... A61K 31/155
[58] Field of Search ........................... 424/327, 326

[56] References Cited
UNITED STATES PATENTS
3,658,993  4/1972  Kodama et al. .................. 424/326

OTHER PUBLICATIONS
Derwent Abstract of Belgian Pat. No. 722136(1968).

*Primary Examiner*—V. D. Turner
*Attorney, Agent, or Firm*—Gerald D. Sharkin; Robert S. Honor; Walter F. Jewell

[57] ABSTRACT

Substituted benzylidene hydrazines e.g. N-(4-phenyl-benzylidene)-N'-amidino hydrazine and their use as hypoglycemic-antihyperglycemic agents, anti-obesity agents and anti-inflammatory agents.

2 Claims, No Drawings

SUBSTITUTED BENZYLIDENE HYDRAZINES FOR TREATING HYPERGLYCEMIA, OBESITY AND INFLAMMATION

This is a divisional of application, Ser. No. 20,418 filed Mar. 17, 1970 now abandoned, which application is a continuation-in-part of application, Ser. No. 825,412, filed May 16, 1969 now abandoned.

This invention relates to substituted benzylidene hydrazines. More particularly, it relates to novel N-(4-substituted benzylidene)-N' amidino hydrazines and acid addition salts thereof. The invention also relates to the use of these and other substituted benzylidene hydrazines as hypoglycemic-antihyperglycemic agents, anti-obesity agents and anti-inflammatory agents to pharmaceutical compositions containing the compounds as an active ingredient thereof, and the method of using such compositions for the treatment of hyperglycemia, obesity and inflammation.

The active agents with which this invention is concerned may be represented by the following structural formula

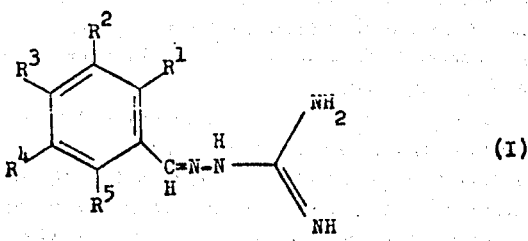

(I)

where
$R^1$, $R^2$, $R^3$, $R^4$ and $R^5$ independently are H, halo having an atomic weight of 19 to 36, trifluoromethyl, phenyl or lower alkyl having 1 to 3 carbon atoms, e.g. methyl, ethyl or propyl, provided that
1. there are no adjacent trifluoromethyl and/or phenyl groups,
2. at least one of $R^1$, $R^2$, $R^3$, $R^4$ or $R^5$ must be other than H,
3. $R^1$, $R^2$ or $R^4$ is not trifluoromethyl when $R^1$, $R^2$, $R^4$ or $R^5$ are only H, halo or trifluoromethyl and $R^3$ is H, and
4. both $R^1$ and $R^5$ are methyl only, when $R_2$, $R_3$ and $R_4$ are other than hydrogen.

All of the compounds defined by formula (I) may be prepared by treating a substituted benzaldehyde with an acid addition salt of amidinohydrazine or the free amidino hydrazine. The process may be generally depicted as follows:

where $R^1$, $R^2$, $R^3$, $R^4$ and $R^5$ are as defined above.

In accordance with the above process, the compounds of formula (I) are prepared by treating a benzaldehyde of formula (II) with a free base or acid salt of the amidinohydrazine of formula (III) in solvent such as alcohols, e.g. lower alkanols such as ethanol, isopropanol and the like. The reaction may be carried out at a temperature of from about 75° – 150°C, preferably the reflux temperature of the reaction mixture, for about 8 – 48 hours. The particular solvent and temperatures used are not critical to the successful completion of the reaction. The amidinohydrazine acid additon salts which may be used include the strong mineral acid addition salts, e.g., the hydrogen halides such as the hydrogen chloride, hydrogen iodide or hydrogen bromide, or the carbonate, sulfate and the like. The resulting product is readily recovered by conventional techniques, e.g., filtration. When the product is recovered as an acid addition salt, it may be converted to the free base by standard techniques. When the compound of formula (I) is recovered as the free base it may be readily converted to the acid addition salt from by conventional methods, such as suspending the compound (I) in alcohol or water and treating with the appropriate acid.

Certain of the compounds of formula (II) are known and may be prepared according to methods disclosed in the literature. These compounds of formula (II) not specifically disclosed are prepared according to analogous methods from known materials.

The hypoglycemic-antihyperglycemic activity of the compounds of formula (I) is indicated by their activity in chickens given 10 mg/kg orally of active material and thereafter dosed orally with glucose and blood glucose levels compared with those obtained with chickens given placebo and glucose alone.

The anti-obesity activity of the compounds of formula (I) is indicated by their activity in Male Wistar rats dosed orally with 11 mg/kg of active material after at least 20 hours of fasting. One hour after receiving the drug the animal is sacrificed and the upper small intestine is removed and washed with glucose-saline. A 5cm section of the intestine is everted so that the mucosal surface is on the outside. One end of the segment is tied off and the center of the sac so formed, is filled with oxygen saturated Kreb's biocarbonate buffer. The other end is then closed to form a sac and the sac is incubated in 10 ml of oxygen saturated biocarbonate buffer for 60 minutes at 37°C. Both the outside and inside solutions contain initially 0.3% of glucose. At the end of the incubation time the glucose content of the

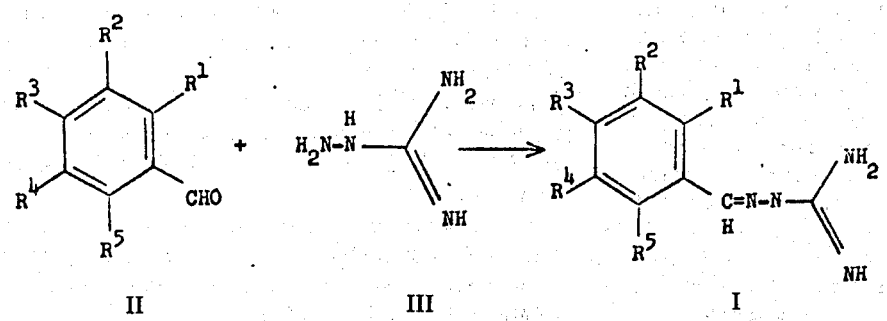

II     III     I outer (mucosal) and the inner (serosal) solution is determined using the standard Autoanalyzer procedure. Similar preparations are prepared simultaneously from animals receiving the vehicle only to serve as controls. The percent inhibition of glucose transport caused by the drug is calculated from the formula.

$$\% I = 100 - ( \frac{ST - MT}{SC - MC} \times 100)$$

where

I equals inhibition
S equals glucose concentration (mg%) of serosal fluid at the end of an experiment
M equals glucose concentration (mg%) of mucosal fluid at the end of an experiment
C equals control animal
T equals drug treated animal The anti-inflammatory activity of the compounds of formula (I) is indicated by their activity in rats given 100 mg/kg of active compound orally and tested using the acute carrageenan-induced edema procedure substantially as described by Winter (Proc. Soc. Exp. Biol., 11, 544, 1962).

As indicated, the compounds of formula (I) are useful as hypoglycemic-antihyperglycemic agents. For such usage, the compounds may be administered orally or parenterally as such or admixed with conventional pharmaceutical carriers. They may be administered orally in such forms as tablets, dispersible powders, granules, capsules, syrups and elixirs, and parenterally as solutions, suspensions, dispersions, emulsions, and the like; e.g., a sterile injectable aqueous suspension. The compositions for oral use may contain one or more conventional adjuvants, such as sweetening agents, flavoring agents, coloring agents and preserving agents, in order to provide an elegant and palatable preparation. Tablets may contain the active ingredient in admixture with conventional pharmaceutically acceptable excipients, e.g. inert diluents, such as calcium carbonate, sodium carbonate, lactose and talc, granulating and disintegrating agents, e.g. starch and alginic acid, binding agents, e.g. starch, gelatin and acacia, and lubricating agents, e.g. magnesium stearate, stearic acid and talc. The tablets may be uncoated or coated by known techniques to delay disintegration and absorption in the gastro-intestinal tract and thereby provide a sustained action over a longer period. Similarly, suspensions, syrups and elixirs may contain the active ingredient in admixture with any of the conventional excipients utilized for the preparation of such compositions, e.g., suspending agents (methylcellulose, tragacanth and sodium alginate), wetting agents (lecithin, polyoxyethylene stearate and polyoxyethylene sorbitan mono-oleate) and preservatives (ethyl-p-hydrobenzoate). Capsules may contain the active ingredient alone or admixed with an inert solid diluent, e.g. calcium carbonate, calcium phosphate and kaolin. The injectable compositions are formulated as known in the art and may contain appropriate dispersing or wetting agents and suspending agents identical or similar to those mentioned above.

Furthermore, these compounds of formula (I) may be similarly administered in the form of their non-toxic pharmaceutically acceptable acid addition salts. Such salts possess the same order of activity as the free base, are readily prepared by reacting the base with an appropriate acid and accordingly are included within the scope of the invention. Representative of such salts are the mineral acid salts, such as the hydrochloride, hydrobromide, sulfate, phosphate and the like and the organic acid salts, such as the succinate, benzoate, acetate, p-toluene-sulfonate, benzene-sulfonate, maleate, malate, tartrate, methanesulfonate, cyclohexylsulfamate and the like.

The dosage of active ingredient employed for the alleviation or prevention of hyperglycemia may vary depending on the particular compound employed and the severity of the condition being treated. However, in general, satisfactory results are obtained when the compounds (I) are administered at a daily dosage of from about 0.1 milligrams to about 40 milligrams per kilogram of animal body weight, preferably given in divided doses two to four times a day, or in sustained release form. For most large mammals, the total daily dosage is from about 4 milligrams to about 25 milligrams. Dosage forms suitable for internal use comprise from about 1 milligram to about 12.5 milligrams of the active compound.

The dosage of active ingredient employed when compounds (I) are used as anti-obesity agents may vary depending on the particular compound employed and the severity of the condition being treated. However, in general, satisfactory results are obtained when the compounds (I) are administered at a daily dosage of from about 1 milligram to about 100 milligrams per kilogram of animal body weight, preferably given in divided doses two to four times a day, or in sustained release form. For most large mammals, the total daily dosage is from about 10 milligrams to about 400 milligrams. Dosage froms suitable for internal use comprise from about 2.5 milligram to about 200 milligrams of the active compound.

The dosage of active ingredient employed when compounds (I) are used as anti-inflammatory agents may vary depending on the particular compound employed and the severity of the condition being treated. However, in general, satisfactory results are obtained when the compounds (I) are administered at a daily dosage of from about 1 milligram to about 100 milligrams per kilogram of animal body weight, preferably given in divided doses two to four times a day, or in sustained release form. For most large mammals, the total daily dosage is from about 10 milligrams to about 400 milligrams. Dosage forms suitable for internal use comprise from about 2.5 milligram to about 200 milligrams of the active compound.

The preferred pharmaceutical compositions from the standpoint of preparation and ease of administration are solid compositions, particularly hard-filled capsules and tablets.

The following examples are provided for the purpose of illustration and not by way of limitation. They are not intended so as to limit the scope of the invention as defined in the appended claims.

EXAMPLE 1

N-(2,6-dichlorobenzylidene)-N'-amidino hydrazine

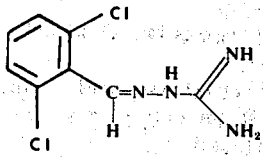

A mixture of 8.8 g (0.05 mole) of 2,6-dichlorobenzaldehyde, 6.8 g (0.05 mole) amidinohydrazine (amino guanidine) carbonate and 150 ml of ethanol is stirred and refluxed for 18 hours. The clear solution is cooled to room temperature and the resultant solid is filtered off to give N-(2,6-dichlorobenzylidene)-N'-amidino hydrazine; m.p. 237°–238°C with decomposition.

EXAMPLE 2

Following the conditions of Example 1 and in place of 2,6-dichlorobenzaldehyde, starting with
  a. 2-chlorobenzaldehyde
  b. 2-fluorobenzaldehyde
  c. 2,6-difluorobenzaldehyde
  d. 2-chloro-6-fluorobenzaldehyde
  e. 2-fluoro-4-chlorobenzaldehyde
  f. 4-phenylbenzaldehyde
  g. 3,4-dichlorobenzaldehyde
  h. 2,4,6-trichlorobenzaldehyde,
  i. 4-trifluoromethylbenzaldehyde
  j. 4-methylbenzaldehyde;
the following products are obtained:
  a. N-(2-chlorobenzylidene)-N'-amidino hydrazine
  b. N-(2-fluorobenzylidene)-N'-amidino hydrazine, m.p. 187°–189°C
  c. N-(2,6-difluorobenzylidene)-N'-amidino hydrazine
  d. N-(2-chloro-6-fluorobenzylidene)-N'-amidino hydrazine
  e. N-(2-fluoro-4-chlorobenzylidene)-N'-amidino hydrazine m.p. 221°–223°C
  f. N-(4-phenylbenzylidene)-N'-amidino hydrazine, m.p. 233°–235°C
  g. N-(3,4-dichlorobenzylidene)-N'-amidino hydrazine, m.p. 178°–180°C
  h. N-(2,4,6-trichlorobenzylidene)-N'-amidino hydrazine, m.p. 245°–246°C
  i. N-(4-trifluoromethylbenzylidene)-N'-amidino hydrazine
  j. N-(4-methylbenzylidene)-N'-amidino hydrazine.

Compound 2(c) : N-(2,6-difluorobenzylidene)-N'-amidino hydrazine was suspended in water and treated with hydrochloric acid to form the hydrochloride salt N-(2,6-difluorobenzylidene)-N'-amidino hydrazine hydrochloride (m.p. 200°–202°C).

EXAMPLE 3

Tablets

Tablets suitable for oral administration which contain the following ingredients may be prepared by conventional tabletting techniques. Such tablets are useful in treating hyperglycemia, obesity and inflammation at a dose of one tablet 2 to 4 times a day.

| Ingredient | Parts by weight |
|---|---|
| N-(4-phenylbenzylidene)-N'-amidino hydrazine | 10 |
| tragacanth | 2 |
| lactose | 79.5 |
| corn starch | 5 |
| talcum | 3 |
| magnesium stearate | 0.5 |

EXAMPLE 4

Dry filled capsules

Capsules suitable for oral administration which contain the following ingredients are prepared in a conventional manner. Such capsules are useful in treating hyperglycemia, obesity, and inflammation at a dose of one capsule 2 - 4 times a day.

| Ingredient | Parts by Weight |
|---|---|
| N-(4-phenylbenzylidene)-N'-amidino hydrazine | 10 |
| Inert solid diluent (starch, lactose, kaolin) | 10 |

EXAMPLE 5

Sterile Solution for Injection

The following ingredients are dissolved in water for injection. The resulting solution is filtered through an appropriate medium to render a clear solution. The solution is then autoclaved to render it sterile.

| Ingredient | Parts by Weight |
|---|---|
| N-(4-phenylbenzylidene)-N'-amidino hydrazine | 10 |
| sodium alginate | 0.5 |
| buffer system | as desired |
| lecithin | 0.5 |
| sodium chloride | as desired |
| water for injection | to desired volume |

EXAMPLE 6

The following formulations for syrups or elixirs containing an effective amount of active compound may be formulated using conventional methods.

| | Parts by Weight | |
|---|---|---|
| | syrup | elixir |
| N-(4-phenylbenzylidene)-N'-amidino hydrazine | .5 – 3.5 | .5 – 3.5 |
| buffering system | quantity sufficient to adjust pH | |
| sodium benzoate | .1 – .5 | .1 – .5 |
| flavoring agent | .01 – 2 | .01 – .2 |
| water | 20 – 40 | 5 – 20 |
| simple syrup U.S.P. | 30 – 70 | 0 |
| sorbitol solution (70%) | 10 – 30 | 20 – 60 |
| certified dye | .5 – 2 | .5 – 2 |
| alcohol | 0 | 2.5 – 20 |
| methyl paraben | 0 | .05 – .1 |
| propyl paraben | 0 | .05 – .1 |
| sodium cyclamate | 0 | .1 – .4 |
| sodium saccharin | 0 | .01 – .04 |

What is claimed is:

1. A method of treating hyperglycemia, obesity and inflammation which comprises administering to a mammal in need of said treatment orally or parenterally an anti-hyperglycemic, an anti-obesity or an anti-inflammatory effective amount of a compound of the formula:

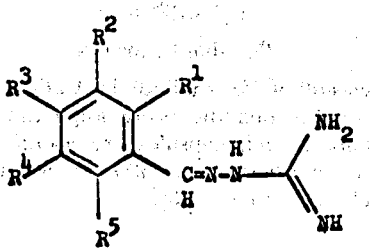

where
R¹, R², R³, R⁴ and R⁵ are H, halo having an atomic weight of 19 to 36, trifluoromethyl, phenyl or lower alkyl, provided that
1. there are no adjacent trifluoromethyl or phenyl groups,
2. at least one of R¹, R², R³, R⁴ or R⁵ must be other than H,
3. R¹, R² or R⁴ is not trifluoromethyl when R¹, R², R⁴ or R⁵ are only H, halo or trifluoromethyl and R³ is H, and
4. both R¹ and R⁵ are methyl, only, when R², R³ and R⁴ are other than hydrogen, or a pharmaceutically acceptable acid addition salt thereof.

2. A method according to claim 1 wherein the compound is administered at a daily dose of from about 4 milligrams to about 400 milligrams.

* * * * *